(12) United States Patent
Shelton et al.

(10) Patent No.: US 6,847,940 B1
(45) Date of Patent: Jan. 25, 2005

(54) SYSTEM AND METHODS FOR PROVIDING A HEALTH CARE INDUSTRY TRADE SHOW VIA INTERNET

(76) Inventors: John S. Shelton, 6555 Quince, Ste # 501, Memphis, TN (US) 38119; H. Stephen Brown, 1661 Int'l Place Dr. Ste # 300, Memphis, TN (US) 38120

( * ) Notice: Subject to any disclaimer, the term of this patent is extended or adjusted under 35 U.S.C. 154(b) by 498 days.

(21) Appl. No.: 09/594,739

(22) Filed: Jun. 16, 2000

(51) Int. Cl.[7] ............................................... G06F 17/60
(52) U.S. Cl. ........................................................ 705/26
(58) Field of Search .................................... 705/26, 27

(56) References Cited

U.S. PATENT DOCUMENTS

| | | | |
|---|---|---|---|
| 4,980,829 A | | 12/1990 | Okajima et al. |
| 5,490,061 A | * | 2/1996 | Tolin et al. ..................... 704/2 |
| 5,784,546 A | * | 7/1998 | Benman, Jr. ............. 707/500.1 |
| 5,809,247 A | * | 9/1998 | Richardson et al. ........ 709/218 |
| 6,009,410 A | | 12/1999 | LeMole et al. |
| 6,020,884 A | | 2/2000 | MacNaughton et al. |
| 2001/0014865 A1 | | 8/2001 | Franke |

OTHER PUBLICATIONS

No Author, "Medtrade online at www.medtrade.com; The official healthcare industry virtual trade show site to be available on SEMCO Productions", Business Wire, Aug. 5, 1996. Retrieved from Dialog File: 16, Acc#:04496026.*
No Author, "American–Academy of Physician Assistants Chooses Avicenna; Avicenna Reaches 32,000 Registered Users", PR Newswire, Sep. 16, 1996. Retrieved from Dialog File: 16, Acc#:04569291.*
No Author, "Netscape and Qwest Unveil Plans For Next–Generation Internet Communications", PR Newswire, Sep. 17, 1998. Retrieved from Dialog File:20, Acc#:02840475.*
"Alpha Bytes Announces H–NET(R): Full–Service E–Commerce Internet Portal for Vision Care Industry", PR Newswired, p. 2288 (Aug. 1999).

* cited by examiner

Primary Examiner—Jeffrey A. Smith
Assistant Examiner—Naeem Haq
(74) Attorney, Agent, or Firm—Reed Smith LLP; Stanley P. Fisher, Esq.; Juan Carlos A. Marquez, Esq.

(57) ABSTRACT

This invention will serve as a new worldwide platform for "business-to-business" and "business-to-participants" tradeshows occurring in the healthcare industry via the Internet 24 hours a day. One embodiment of the invention is a system or method for providing a healthcare industry trade show via internet including at least one personal or network computer for collecting, assembling, storing, correlating, or otherwise processing information desired by a participant of the healthcare industry, and at least one other computer used by the participant of the healthcare industry connected via internet or intranet to conduct transactions with other participants or exhibitors of the healthcare industry trade show. Another embodiment includes at least one of the communication vehicles to be used at the option of the participant of the healthcare industry. Another embodiment provides optional features including a booth with multiple rooms; a tradeshow Concierge; instant audio and/or video announcements via eLERTS; direct selling via detailing; a Pop-Up system of interaction with experts and Attendees on the convention floor; opportunities for participants to gain insights into treatment via presentation of case reports; the use of special advisory panels assessing the needs of participants and create education programs.

127 Claims, 9 Drawing Sheets

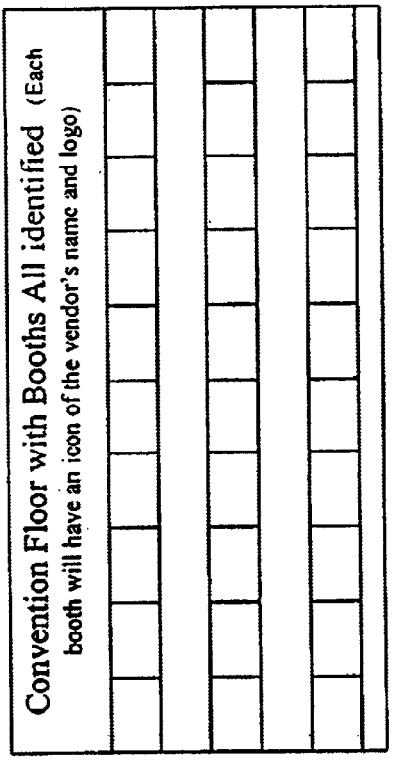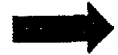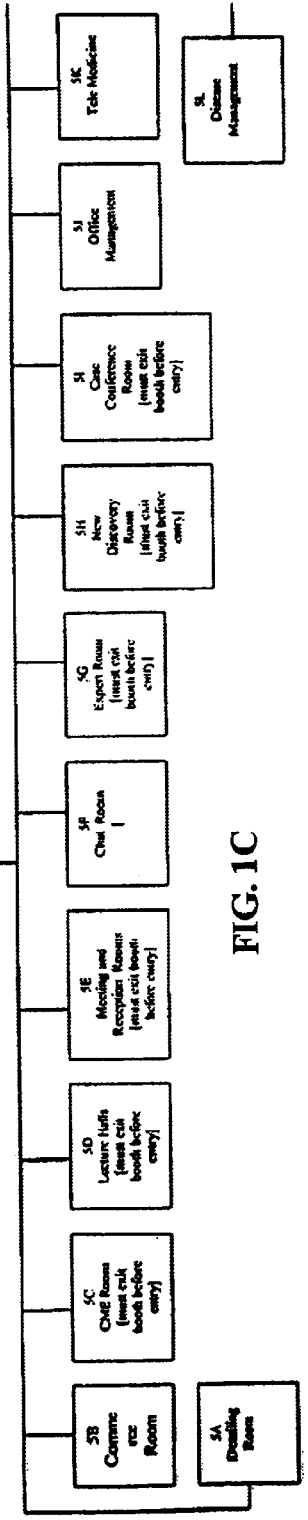
FIG. 1B
FIG. 1C

SYSTEM AND METHODS FOR PROVIDING A HEALTH CARE INDUSTRY TRADE SHOW VIA INTERNET

BACKGROUND OF THE INVENTION

1. Field of the Invention

The invention relates to systems and methods for providing a virtual trade show via internet for healthcare professionals. More particularly, the invention relates to systems and methods providing via internet a virtual trade show for the participants in the healthcare industry, including the participants of any healthcare trade shows, seminars, conferences, etc., especially healthcare professionals.

2. Discussion of the Related Art

A variety of healthcare data management systems have been developed for improving the delivery of healthcare such as U.S. Pat. No. 5,542,420 entitled "Personalized Method and System for Storage, Communication, Analysis, and Processing of Health-Related Data" to Goldman et al. on Aug. 6, 1996 for a personalized prescription as to edibles, U.S. Pat. No. 5,940,802 entitled "Digital Disease Management System" to Hildebrand, et. al. on Aug. 17, 1999 for improving the delivery of healthcare for patients, and U.S. Patent No. 5,301,105 entitled "All Care Health Management System" to Cummings, Jr. on Apr. 5, 1994 for providing a closed network among insurers and healthcare providers to better manage healthcare utilization and reimbursements. As internet is getting more popular and secured by modern technologies, more such information systems further included an internet-transmitting feature, such as U.S. Pat. No. 5,890,129 to Spurgeon on Mar. 30, 1999, entitled "System for Exchanging Healthcare Insurance Information".

As more individual data management systems or virtual sites[1] have been developed for healthcare practitioners, health management organizations, pharmaceutical companies, medical equipment, device and testing manufacturers and suppliers, consumers healthcare products manufacturers. etc. to cover increasing healthcare information in, different therapeutic categories, it becomes increasingly difficult for a member of the healthcare industry to find the desired materials in the flood of information. Therefore, most participants still go to visit expensive and time-consuming trade shows, professional conferences, and continuing educational seminars to accomplish their own pre-set agenda as well as explore interactively with other participants to obtain desired information. From the transactional perspective, trade shows facilitate face-to-face contact, promotional sales information, and in some cases actual sales.

[1] There are many virtual sites related to healthcare, such as "Virtual Medical Center—Martindale's Health Science Guide" at http://www-sci.lib.uci.edu/HSG/Medical.html, but not a virtual healthcare trade show site designed for B2B.

In addition, many trade shows emphasize a specific sector or geographic area of the worldwide healthcare industry to educate, promote products and services and promote sales.

In view of the role of trade shows as above-outlined, many companies have attempted to produce a similar environment over the web to take advantage of its low-cost and convenient worldwide entry, and its ease of operation. For example, the Healthcare Convention and Exhibitors Association hosts a site at http://www.hcea.org/[2], which Association brings together trade show designers, city and state convention centers and other groups involved in designing, hosting and providing production services to a trade show. The site also solicits participants for a traditional trade show for conventional services to be held in June 2000 in Savannah. Both the exhibitors of the booths and the Attendees to this site will be different from the exhibitors and Attendees of the trade show of the present invention. In hcea.org, the exhibitors are cities desiring to host a trade show, designers of and purchasers booths, manufacturers of booths and the Attendees are trade show planners advertising agencies and often designers of tradeshow exhibits and booths. As another example, although "American Medical Review Online Tradeshow" http://tradeshows-online.com/americanmedical/html/exhibitionhall.htm[3] offers consumers, not participants of the healthcare industry, each show booth with an introduction video, textual and graphic descriptions of the products or services, an e-mail message box, and a link to the seller's webpage, the booths are simply characterized by products, services, and alternative medicine. The above-mentioned two sites are consumer-oriented, namely business-to-consumer (B2C). In addition, both of the above-mentioned sites have data structures and functions that are overly-simplified and so limited that they can hardly help anyone obtain his/her desired information efficiently. U.S. Pat. No. 5,966,130 titled "Integrated Virtual Networks" to Benman, Jr. on Oct. 12, 1999 describes a system allowing a participant to attend a trade show as it happens with live or virtual imagery. However, it fails to provide many characteristics of a traditional trade show desired by the participants of the healthcare industry.

[2] As visited on Jun. 13, 2000.
[3] As visited on Jun. 13, 2000.

Currently, there is not a healthcare tradeshow facilitating a business-to-business e-commerce platform for the healthcare participants to allow healthcare manufacturers and suppliers of products and services to provide content, community and commerce to healthcare providers including, but not limited to physicians, doctors, dentists, nurses, veterinarians, pharmacists, managed care organizations, insurers, pharmacy benefit managers, clinics, nursing homes, hospitals, specialty pharmacy networks, pharmacies, drug wholesalers, medical schools, veterinary schools and dental schools.

SUMMARY OF THE INVENTION

It is a purpose of this invention to provide members of the worldwide healthcare industry 24-hour access to healthcare manufacturers and healthcare suppliers of products and services to provide content, community and commerce, . . . via internet real time (live) or virtually without either visitors or exhibitors required to travel or maintain a physical presence for sales, marketing or exchanging technical or market knowledge.

It is another purpose of this invention to provide easily searchable information categories for a healthcare industry visitor to obtain his/her desired information efficiently except for those intentionally blocked or access-limited via verification or authorization procedures.

It is another purpose of this invention to provide a virtual environment where one group of participants may encounter other participants who would not interact with one another but for the existence of this internet healthcare trade show.

It is another purpose of this invention to present relevant information and internet content about products and services, including textual, graphic, and audio description, vital transactional and credit information to facilitate electronic business-to-business (B2B) and business-to-participants of the healthcare industry (B2P) transactions of healthcare products or services. Necessary security measures will be taken to protect proprietary information.

It is another purpose of this invention to verify the authentication of the Attendee. It is another purpose to verify the credit of the Attendee on certain transactions, activities or services.

It is another purpose of this invention to provide feedback about the quality of products/services and information based on the participants' evaluations, etc.

It is another purpose of this invention to actively promote or market products/services to any participant in countries with or without sufficient internet infrastructure. The web host in countries without sufficient internet infrastructure may take risk as well as commission for such activities based on agreements.

It is still another purpose of this invention to provide Attendees with customized online distance learning or telemedicine arrangements.

It is still another purpose of this invention to provide state of the art video-conferencing to ensure Attendees get the real sense of live participation.

It is still another purpose of this invention to attract healthcare experts from around the world to play an integral role in the planning of the trade show's scientific presentations. There is no such international forum in existence today and the procedure will provide a unique opportunity for Attendees to the site to benefit from the experience and insight of these experts.

It is still another purpose of this invention to foster global commerce between exhibitors and Attendees by providing a platform in which to showcase medical products and services, medical institutions, clinics and facilities in different parts of the world. Via digital technology Attendees to the site can directly see and learn about unique treatment environments, procedures, and personnel in locations far from their home base.

It is still another purpose of this invention to virtually detail healthcare products and services, including prescription drugs to healthcare professional Attendees over the Internet.

It is still another purpose of this invention to virtually provide over the Internet continuing medical information to healthcare professionals from an Internet site not controlled or influenced by any manufacturers of medical equipment, devices, or pharmaceutical products.

It is still another purpose of this invention to have a virtual concierge or helper that will assist the Attendees determine the Attendees' special interest, help the Attendees register, help the Attendees find specific information, locations, or areas of interest within the trade show and to provide the Attendees with a history of any previous visit.

It is still another purpose of this invention to provide Attendees information regarding special disease states, conditions or specialties.

It is still another purpose of this invention to provide Attendees an update on what is new at the trade show, since the Attendees' last visit.

It is still another purpose of this invention to provide Attendees with the information regarding specific products or services.

It is still another purpose of this invention while welcoming the participant to the trade show to provide one or more promotional messages or other information.

It is still another purpose of this invention to allow Attendees access to experts.

It is still another purpose of this invention to have such trade show features that include satisfaction surveys, request for suggestions on improvements, information on current continuing education programs, information on future continuing education programs that may be of interest to the Attendee, tracking receipts of goods and services and continuing education credits, request e-mails on various topics, including, but not limited to, documents or information that may be related to areas that such Attendees visited.

BRIEF DESCRIPTION OF THE DRAWINGS

The foregoing and other objects, features and advantages of the invention will become apparent from the following more particular description of preferred embodiments of the invention, as illustrated in the accompanying drawings, in which.

DESCRIPTION OF THE PREFERRED EMBODIMENTS

Figure 1A:
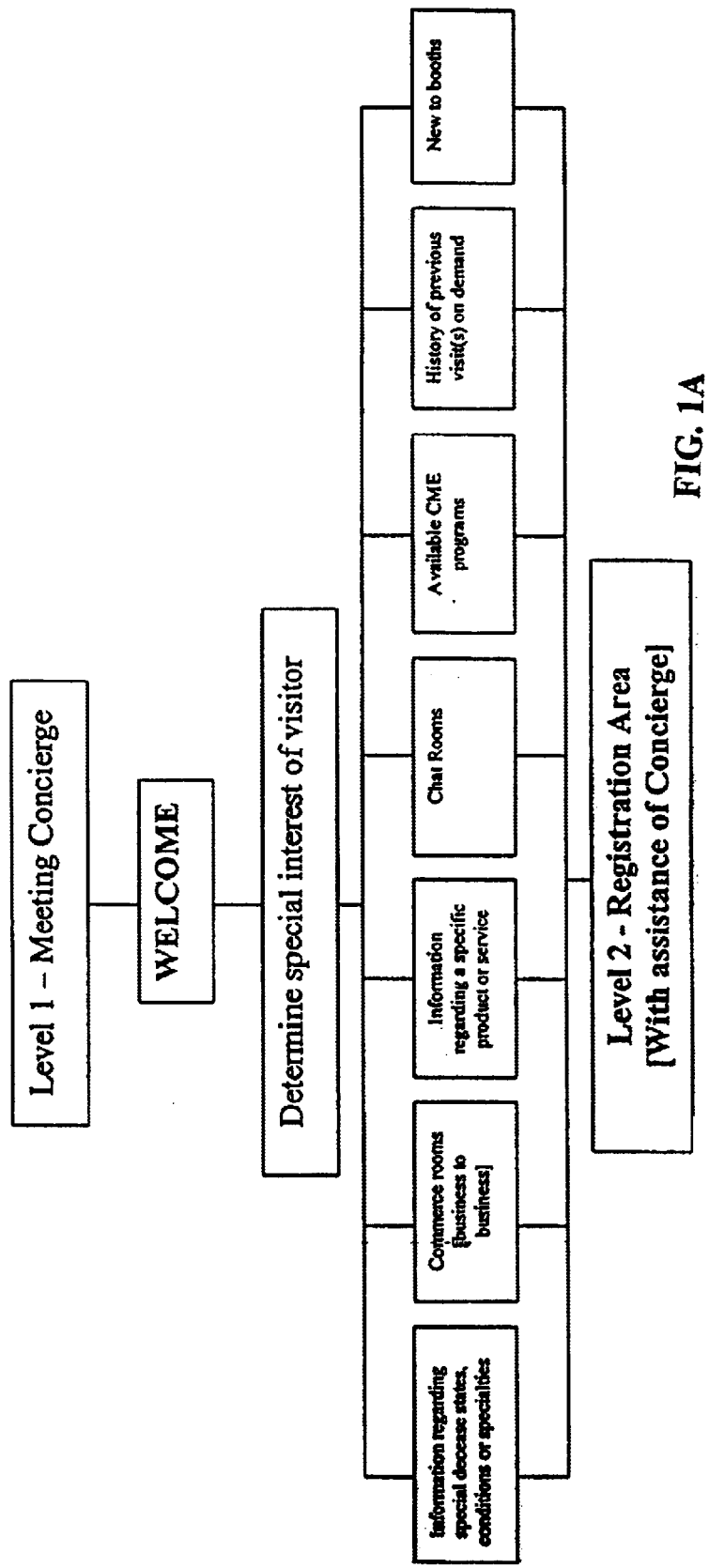
FIG. 1 is a diagram illustrating one embodiment of the process flow of selected access levels of the present invention when deployed in a virtual trade show environment.

In order to more clearly and concisely describe the subject matter of the claims, the following definitions are intended to provide guidance as to the meanings of specific terms used in the following written description. Also it is to be understood that the phraseology or terminology employed herein is for the purpose of description and not of limitation. As used herein:

"Healthcare":[4] The prevention, treatment, and management of illness and the preservation of mental and physical well-being through the services offered by the medical and allied health professions.

[4] The American Heritage® Dictionary of the English Language. Third Edition copyright © 1992 by Houghton Mifflin Company.

"Healthcare industry" includes the industries of or relating to healthcare.

"Participants of the healthcare industry" include but not limited to individual healthcare providers further including but not limited to physicians, osteopaths, dentists, veterinarians (Vets), optometrists, podiatrists, providers of homeopathic medicine, physician assistants, nurses, residents, pharmacists and psychologists; institutional healthcare providers further including but not limited to medical and nursing schools, hospitals, clinics, diagnostic and treatment centers, health maintenance organizations (HMO) and preferred provider organizations (PPO); pharmaceutical companies; medical equipment, device and testing manufacturers and suppliers; job recruiters; consumers of healthcare products and services; managed care organizations; pharmacy benefit managers healthcare consultants; pharmacoeconomics and formulary managers, etc.

"Attendee" includes participants of the healthcare industry who visit the trade show.

"Exhibitors" are the sponsors of the virtual booths and are generally pharmaceutical manufacturers or medical equipment or device manufacturers or suppliers, consumer healthcare products manufacturers or suppliers, health management organizations, health insurance companies, healthcare providers, and managed care organizations.

Health Maintenance Organization (HMO): A managed care organization that arranges a wide spectrum of healthcare services which commonly include hospital care, physicians' services and many other kinds of healthcare services with an emphasis on preventive care.[5]

[5] Glossary of Healthcare Terms, http://www.cigna.com/healthcare/glossary.html visited on Jun. 4, 2000.

Preferred Provider Organization (PPO): A network of healthcare providers which provide managed care to patients with generally higher benefit coverages and lower deductibles.[6]

[6] See ibid.

"Communication Vehicles" include a variety of channels for communication during the visit to the Medtradeshow as well as after the Attendees leaves the site. These vehicles for transmitting textual, 2-D, or 3-D imagery signals will include but are not limited to e-mail, ICQ, IRC, animation or virtual reality which may then be carried via pagers, internet telephony, telephone, satellite, public utility lines, fiber optics and cable. Communication Vehicles will support the functions of concierge, eLERTS (instant audio or video announcements), detailing, celebrity Pop-Ups, Case conferencing, Tele-Medicine, Continuing Education, Advisory Panel, Needs Assessment, Office Management, and/or Disease Management.

ICQ: ("I Seek You") A conferencing program for the Internet which provides interactive chat, e-mail and file transfer and can alert you when someone on your predefined list has also come online.[7]

[7] Tech Encyclopedia, http://www.techweb.com/encyclopedia/ visited on Jun. 4, 2000.

IRC, Internet Relay Chat: Computer conferencing on the Internet. There are hundreds of IRC channels on numerous subjects that are hosted on IRC servers around the world. After joining a channel, your textual or graphical messages are broadcast to everyone listening to that channel.[8]

[8] See ibid.

"Medtradeshow" is a description of the invention; provided, however, any descriptive phrases or domain names may be used for the invention, a virtual healthcare trade show, including but not limited to Medtradeshow.

"DEA" is the abbreviation of the "Drug Enforcement Administration"[9] under the U.S. Department of Justice which is responsible for enforcing the controlled substances laws and regulations of the United States and assigns a provider number to all authorized medical prescribers of controlled drugs.

[9] http://www.usdoj.gov/dea/.

"Enterprise Data Access" and "EDA" Popular middleware software from information builders that runs on more than 35 platforms and provides a common interface between client requests to more than 80 different database and file types. It allows queries on different types of databases at the same time.[10]

[10] See Id.

"Artificial Intelligence" implies human-like intelligence. Devices and applications that exhibit human intelligence and behavior including robots, expert systems, voice recognition, natural and foreign language processing. It also implies the ability to learn or adapt through experience.[11]

[11] See id.

Medtradeshow will serve as a new platform for "business-to-business" and "business-to-Attendees" tradeshows occurring in the healthcare field via the Internet. The basis for Medtradeshow has been the worldwide explosion in the amount of health-related information, products, and services that are now available to the marketplace. One effect of this increase is the inability of healthcare providers to receive and process this data in a timely fashion.

One traditional way to gain exposure to information, products, and services is to attend a tradeshow where one can learn about products and services and also attend educational lectures and courses. Unfortunately attending tradeshows is difficult for most healthcare providers for travel and lodging is expensive and professional and personal demands leave little time to attend these sessions. In addition all of these tradeshows are held thousands of miles away from the majority of those who would attend if they had a more immediate access. It is also ironic that while technology is changing quickly in the healthcare arena most healthcare products/service suppliers are still forced to employ large international sales forces to do a majority of the day-to-day selling.

Medtradeshow provides more efficient ways of both providing information and making the sales function more efficient. Medtradeshow creates a virtual reality via the Internet, where information exchange and/or transactions between healthcare providers and healthcare manufactures, suppliers and experts can occur 24 hours a day, every day of the year. In addition since Medtradeshow is virtual, any healthcare provider with access to a computer and modem can participate, thus eliminating the traditional constraints of time and financial limitations.

Not only does Medtradeshow create a unique environment for "business-to-business" and "business-to— Attendees" transactions, it also provides unique options designed to help those attending the healthcare tradeshow to navigate around the virtual convention floor. These features include a booth with multiple rooms; a tradeshow Concierge; instant audio and/or video announcements via eLERTS; direct selling via detailing; a unique Pop-Up system of interaction with experts and Attendees on the convention floor; opportunities for Attendees to gain insights into treatment via presentation of case reports; the use of special advisory panels to help assess the needs of those visiting the site and create education programs to meet those needs; and instant education credits.

This virtual Medtradeshow provides each Attendee with (1) options to receive information about the content, products and/or services showcased in each booth presented in print, voice, and/or video format; (2) an opportunity to receive the history of each visit. Thus the Attendee will know which booths were visited and what transpired in each booth, thus assisting him/her during their current visit. This virtual Medtradeshow provides each Attendee with the opportunity to receive (1) an email summarizing and highlighting portions of the conference proceedings; (2) an opportunity to learn about products and services; (3) an opportunity to receive the following but not limited to product monographs, to order samples of medications, to obtain reprints of articles from the scientific literature, newsletters, scientific monographs, supplements, audiotapes, videotapes, via the communication vehicles. Specifically, the communication vehicles support textual, 2-D, or 3-D imagery or animation to be displayed at the request of an Attendee. In addition, such communication vehicles support inputted signals via touch screens, keyboards, handwriting recognition, voice recognition means, and other inputting means or their combinations.

As shown in FIGS. 1–10, the present invention incorporates optional functional features, including Concierge, detailing, celebrity Pop-Ups, Case conferencing, Tele-Medicine, Continuing Education, Advisory Panel, Needs Assessment, and Office Management and Disease Management into various Medtradeshow booths, Rooms or Halls to facilitate the above-mentioned functions at different times.

Figure 2:
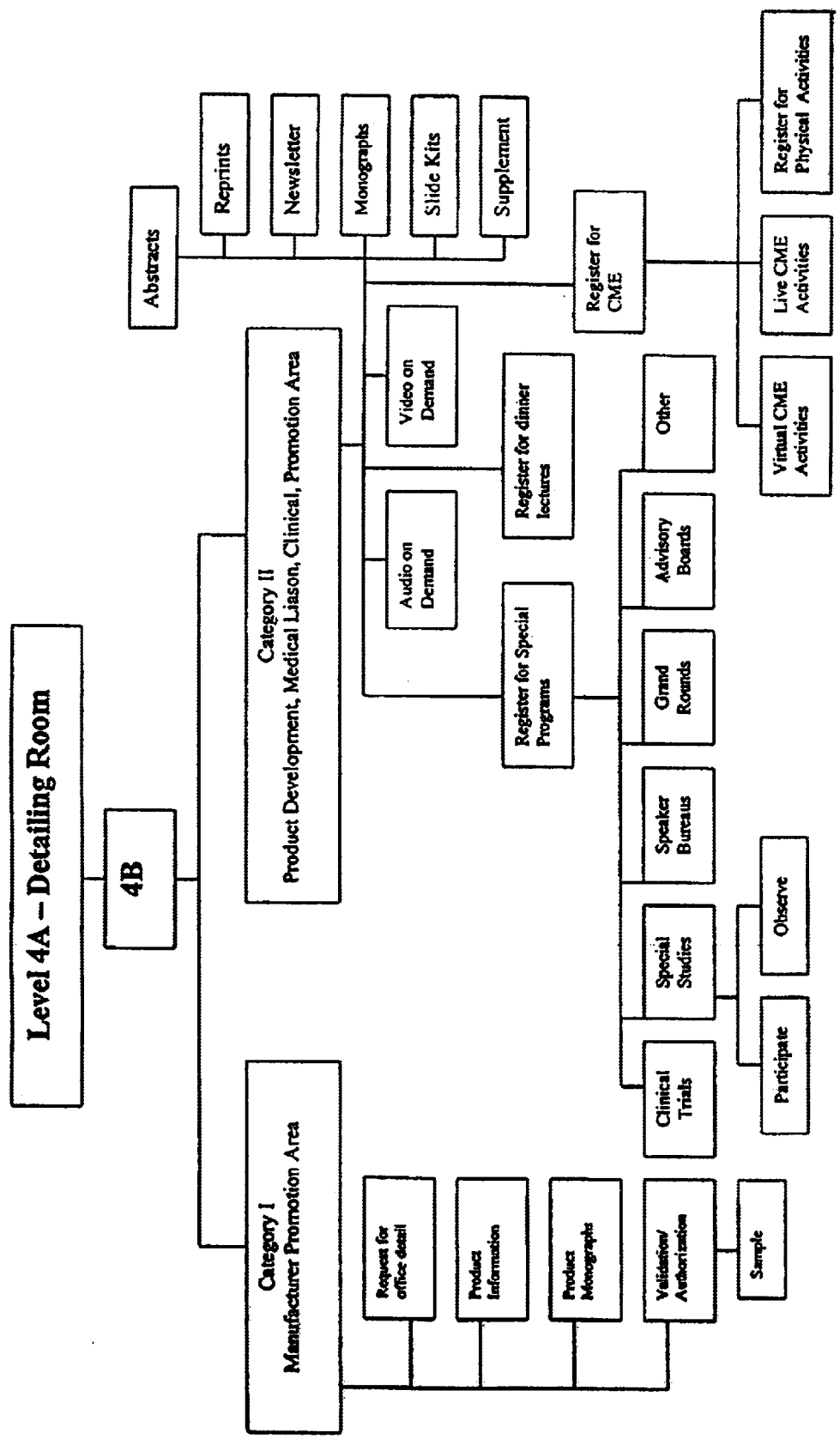
FIG. 2 is a diagram illustrating process flow depicting one embodiment of the detailing feature of the present invention when deployed in a virtual trade show environment.
Figure 3:
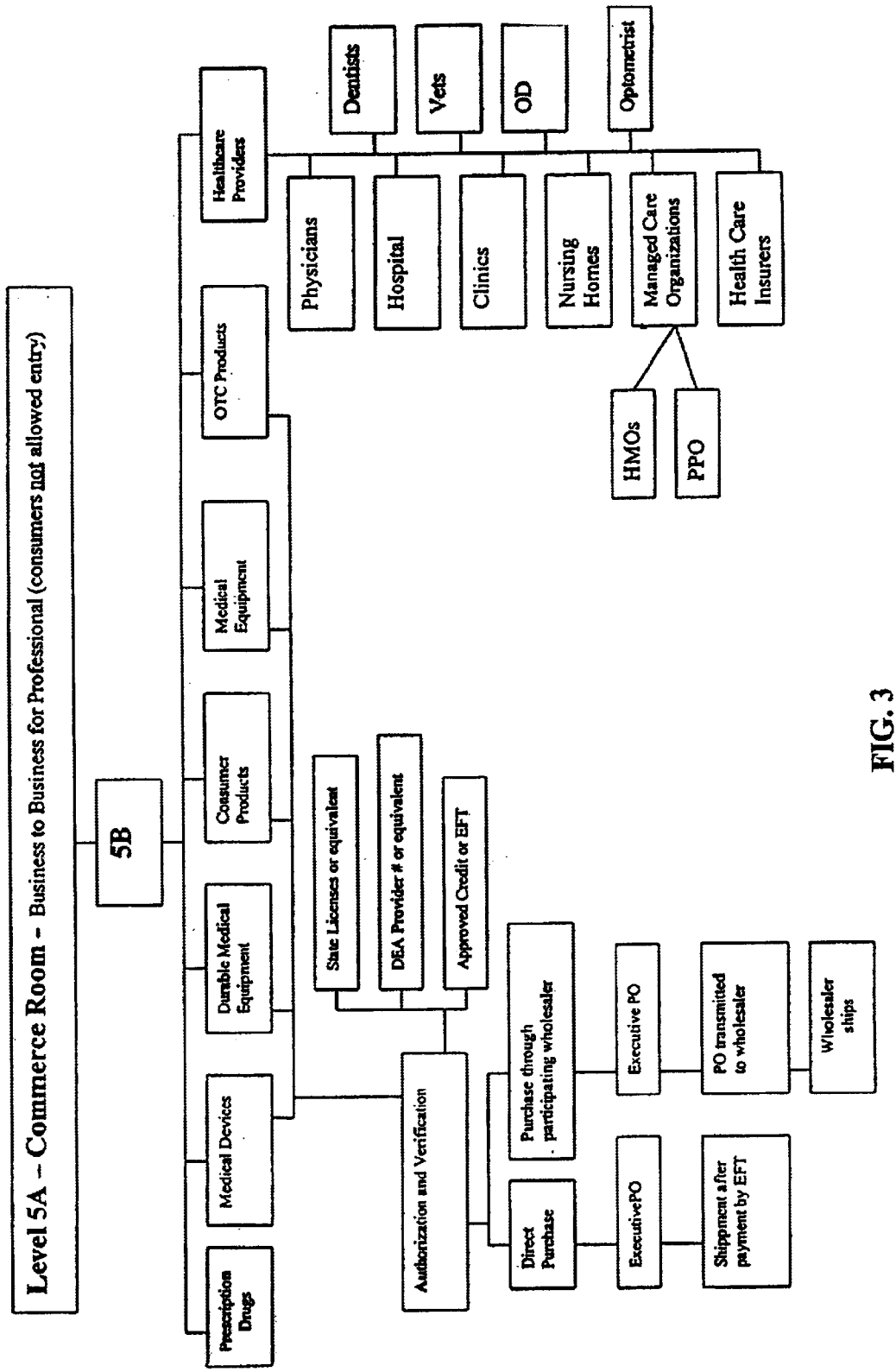
FIG. 3 is a diagram illustrating process flow depicting one embodiment of the Commerce Room feature of the present invention when deployed in a virtual trade show environment.
Figure 4:
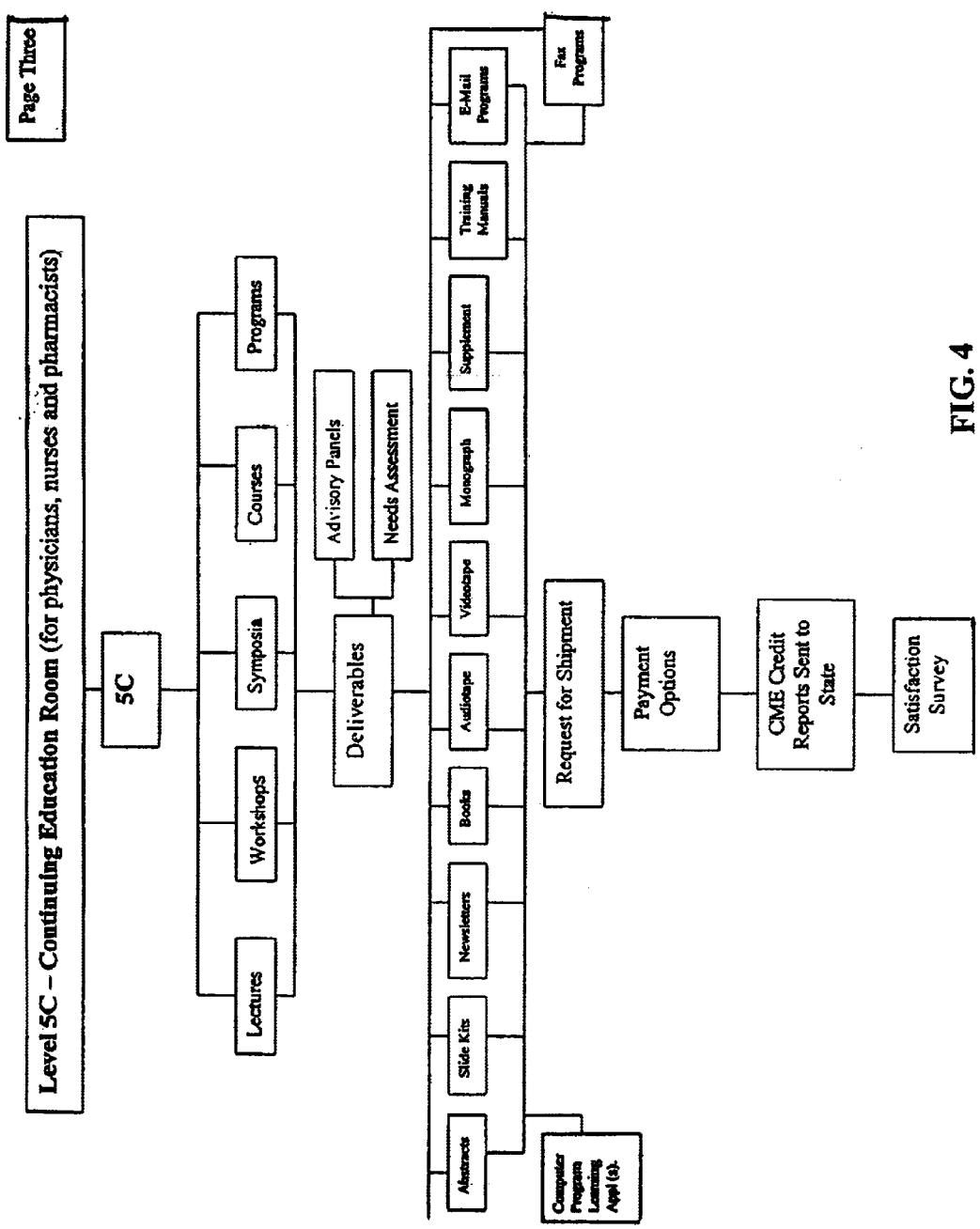
FIG. 4 is a diagram illustrating process flow depicting one embodiment of the Continuing Education Room feature of the present invention when deployed in a virtual trade show environment.
Figure 5:
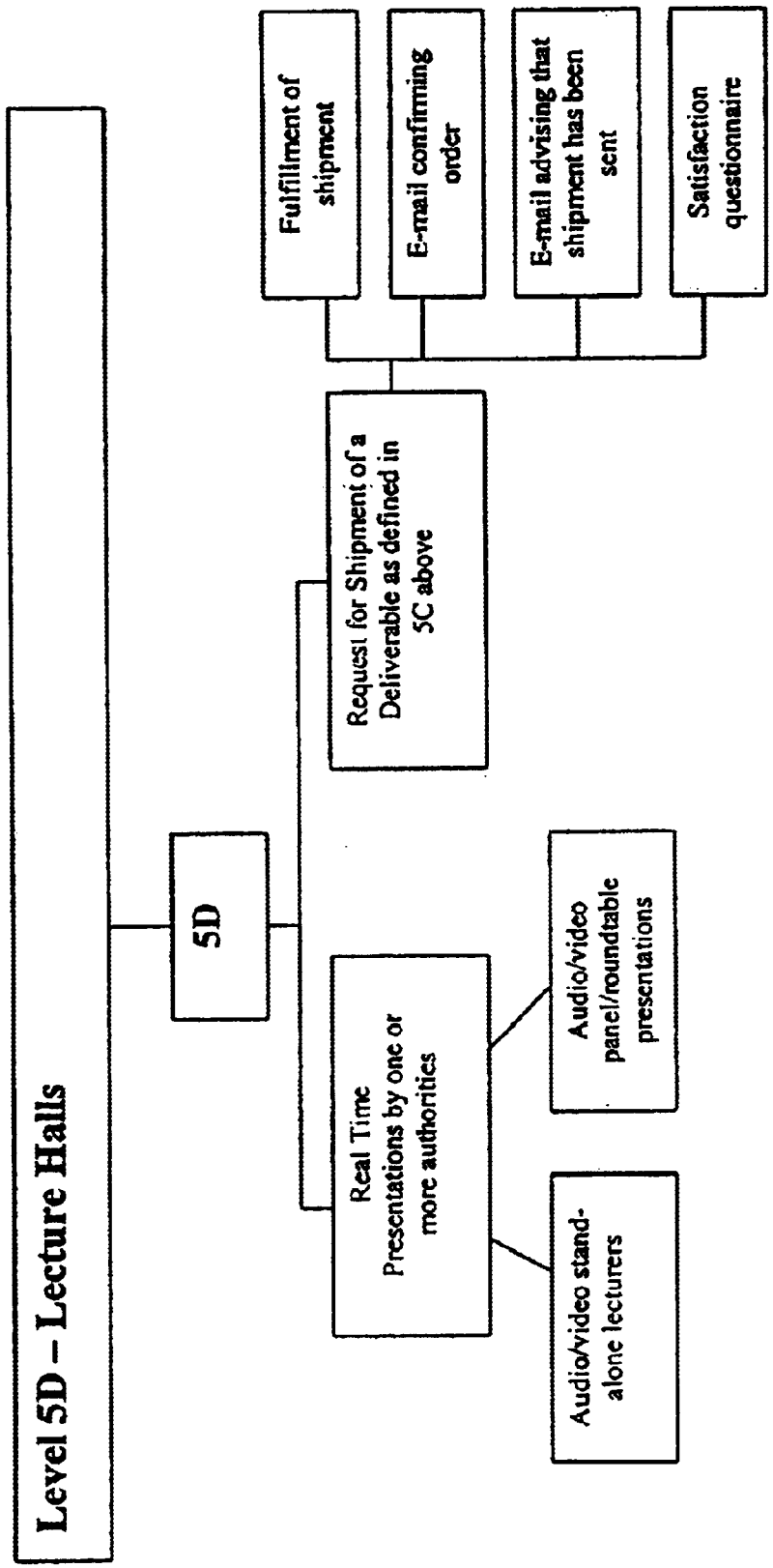
FIG. 5 is a diagram illustrating process flow depicting one embodiment of the Lecture Halls feature of the present invention when deployed in a virtual trade show environment.
Figure 6:
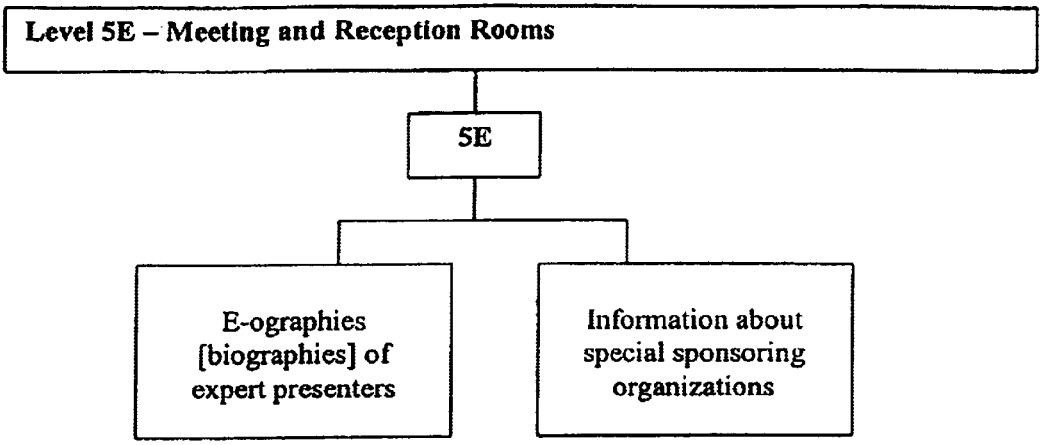
FIG. 6 is a diagram illustrating process flow depicting one embodiment of the Meeting and Reception Room feature of the present invention when deployed in a virtual trade show environment.
Figure 7:
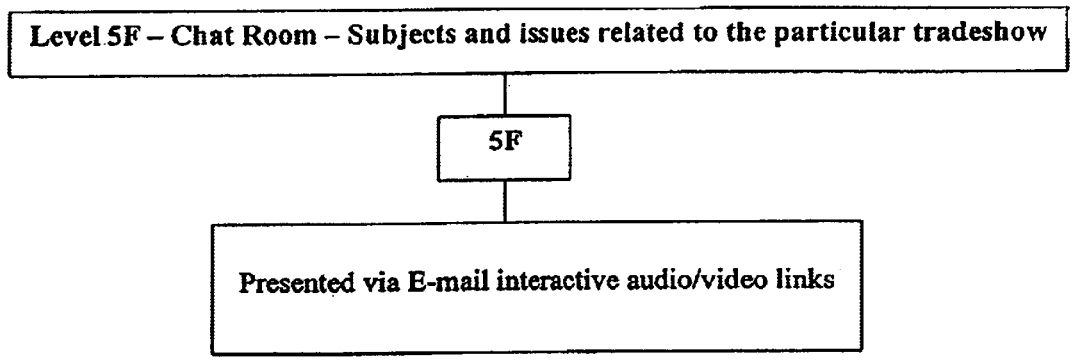
FIG. 7 is a diagram illustrating process flow depicting one embodiment of the Chat Room feature of the present invention when deployed in a virtual trade show environment.
Figures 8, 9:
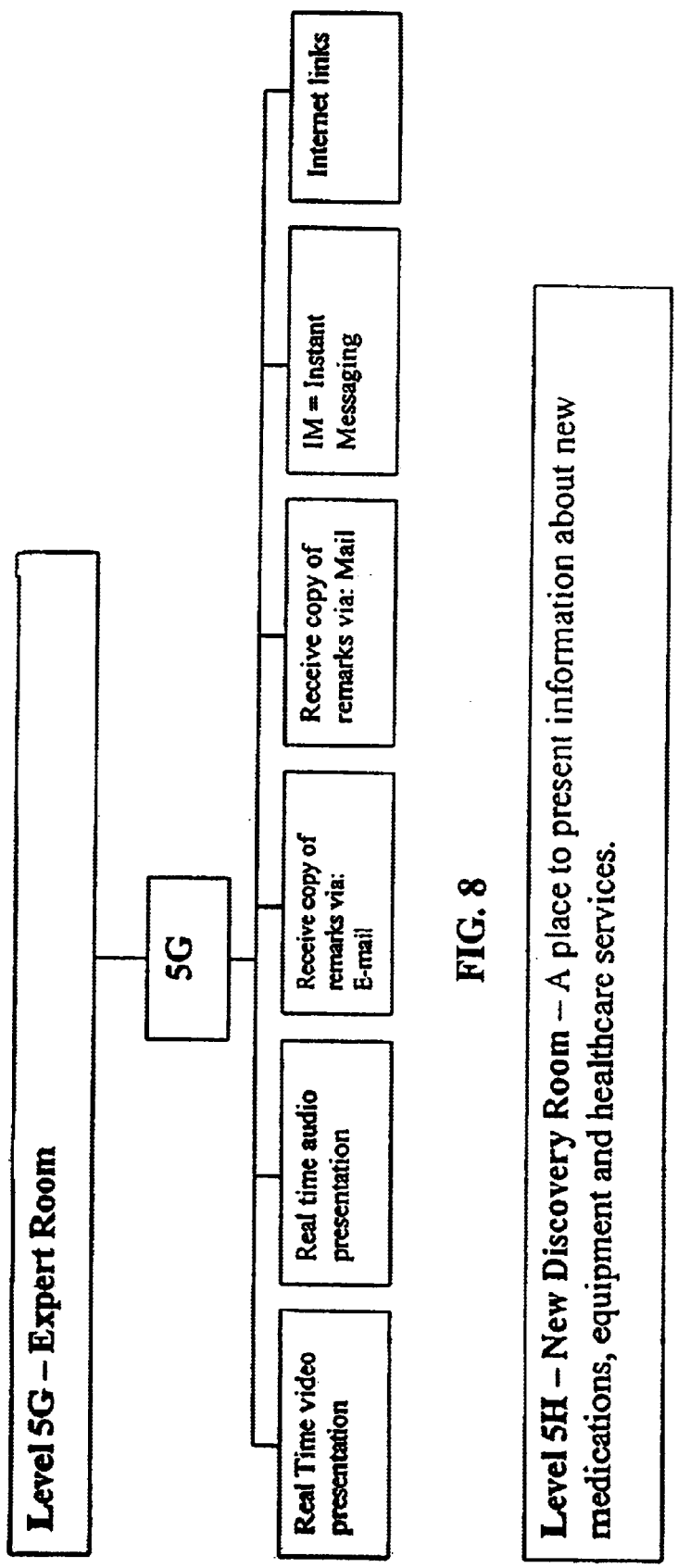
FIG. 8 is a diagram illustrating process flow depicting one embodiment of the Expert Room feature of the present invention when deployed in a virtual trade show environment.
FIG. 9 is a diagram illustrating process flow depicting one embodiment of the New Discovery Room feature of the present invention when deployed in a virtual trade show environment.
Figure 10:
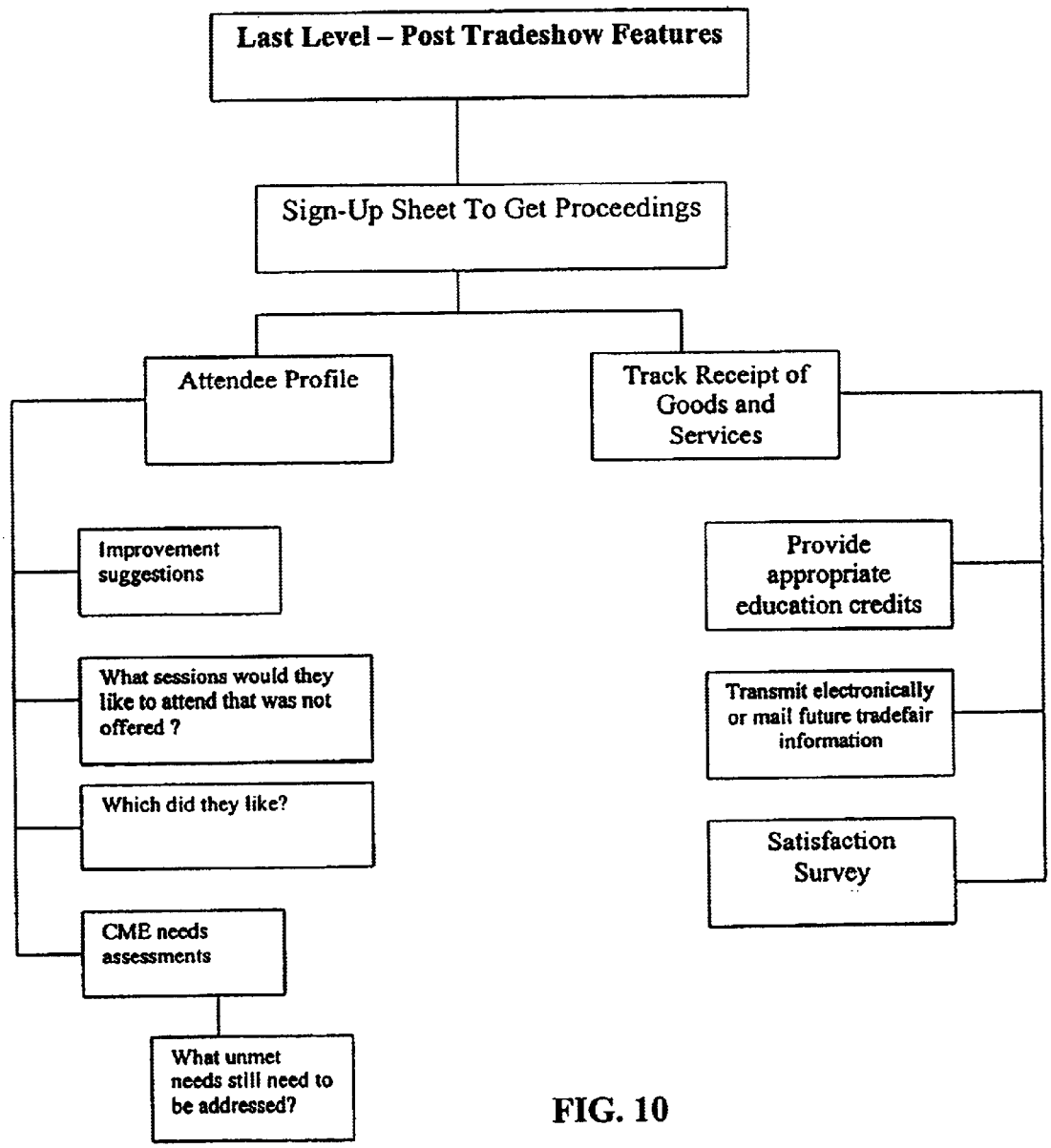
FIG. 10 is a diagram illustrating process flow depicting one embodiment of the Post Medtradeshow feature of the present invention when deployed in a virtual trade show environment.

To ensure each Attendee is appropriately authorized under applicable laws and regulations to access certain rooms or information, verification and authorization procedures are provided whenever and wherever necessary. For example, manufacturers will wish to block certain healthcare professionals who are not appropriately licensed for receiving samples as shown in FIG. 2.

Concierge

The "concierge" feature, as shown in FIG. 1, will include, but not be limited to providing general programmed information about the Medtradeshow and, through a series of prompts provide Attendees with directions to the areas within the various booths where qualified experts will answer specific questions about medications, medical devices, service suppliers and institutions. The virtual concierge will first welcome the Attendee and then provide one or more promotional messages or other information. The virtual concierge will also assist each Attendee, determine the Attendee's special interest, help the Attendee register, help the Attendee find specific information, locations, or areas of interest within the trade show and to provide the Attendee with a history of any previous visit as well as to update on what is new at the trade show, since the Attendee's last visit.

In one embodiment, this concierge is generated by a sophisticated and subtle information storage and retrieval system equipped with artificial intelligence. In other words, the concierge will ask you what help you need and automatically call in the appropriate applications to aid you in solving your problem. For example, a Medtradeshow Attendee may ask the concierge which areas within the various booths would have information about the availability of a particular US medication in a foreign country. Another typical question could be about therapies provided at a particular institution or about a new device for measuring blood sugar. In another embodiment, the concierge may, with appropriate consent of the Attendee, track Attendee's activities while visiting. Such information, with appropriate consent, may be processed then forwarded (complying with Federal and State Privacy and Confidentiality Laws) to certain Medtradeshow exhibitors.

Beside the communication, as stated above, the concierge also collects data by tracking the Attendees' activity since their registration. As the Attendee moves around the Medtradeshow floor their activity is captured. A formal report summarizing the Attendee's movements, including locations, duration of each stay is prepared and under the appropriate circumstances may be transmitted to appropriate Medtradeshow exhibitors (complying with Federal and State Privacy and Confidentiality Laws).

In terms of visual appearance, the concierge may be shown as a FIGURE of any sex, race, height, weight, eye or hair color.

eLERTS

The eLERTS will, in part, be instant messages that drive traffic to specific booths. The eLERTS are designed to grab the attention of the Attendee and their function will include, but not be limited to, providing information about products and services including references to scientific articles about a particular subject, symposia, disease state management information within a specific booth and reasons for an Attendee to stop by such booths. The eLERTS are designed to bring a sense of realism to the site and can be programmed to provide a true virtual experience. The eLERTS can be transmitted by a written instant message or through an instant video presentation. Thus the Attendee may learn of a new product introduction, that a new booth has just been constructed and might be useful to visit, or that a symposium has been cancelled and a new lecture is available.

The eLERT is also designed to be a maintenance program providing continuous communication to those who have attended the Medtradeshow providing information about new booths, lectures, workshops, and symposia. In addition the recipient will have the opportunity to order samples, purchase goods and services and order copies of enduring materials. In addition there will an opportunity to offer suggestions as to future topics to be covered in the scientific programs.

Detailing

DETAILING in the physical world is carried out by a sales representatives who visit with healthcare providers promoting products and services. These sales representatives use support information obtained from formal or informal, official or non-official information sources, including but not limited to medical journals, company data, information from drug trials, expert advisors, information from meetings, product samples, promotional materials, detail tools and detail aids. The inventor proposes to virtually provide the same services to the healthcare provider over the Internet. The inventor has applied for trademark protection for "detailing" [12] to describe virtual healthcare DETAILING.

[12] detailing is different from "e-tailing" defined as 'selling of retail goods on the Internet' at http://www. whatis.com/detailing.htm (visited Jun. 4, 2000). In particular, detailing is synonymous with business-to-business(B2B) or business-to-participants of the healthcare industry (B2P) transactions rather than business-to-consumer (B2C)transactions.

As shown in FIG. 2, healthcare products or services were divided into two categories for marketing purposes: Category I [Manufacturer Promotional Area] includes those that have been approved by the U.S. Food & Drug Administration (FDA) specific disease or condition. And category II [Product Development, Medical Liaison, Clinical, Promotional Area] includes permitted off-label promotions that are scientific and educational in nature that will be disseminated to the medical community via independent third parties ill the formats of clinical trials, special studies, grand rounds, etc. For example, a pharmaceutical manufacturer would not be permitted to compare its products against another manufacturer; however, a scientific journal article appearing in a peer reviewed Medical Journal could be provided to an Attendee. Such scientific article would be available from the Detail Room in Category II, Category I as an example may have Product Information that is approved by the FDA.

For example, if a psychiatrist would like to learn information about the use of a certain psychotropic medication for the treatment of an illness for which it is not marketed, they would be directed to the "Category II" promotion area which is separated from the "Category I" area. In this promotion area, they would receive scientific information derived from reports in medical journals, meetings, poster presentations, and other sources.

Grand Rounds Room

Interactive grand rounds will be moderated by distinguished experts for physicians, medical students and other selected health professionals. At these sessions actual cases will be discussed and the experts will explain their suggested diagnosis and treatment alternatives.

Speaker Bureaus Room

In this room healthcare providers have the opportunity to offer their services to talk with their colleagues about the diagnosis and treatment of a particular disease.

Celebrity "Pop-Up" Mechanism/Expert Room

"Celebrity Pop-Up" allows spontaneous interaction between subject experts and Medtradeshow Attendees. This interaction will occur when the experts randomly pop-up on the Medtradeshow floor to talk with the Attendees. When these chance meetings occur the Attendee can choose from a series of programmed questions to ask the expert. The virtual Medtradeshow provides each Attendee with an opportunity to meet scientific experts via e-mail, ICQ, real time audio or video presentations in selected language(s). The subject matter for these questions will be based on timely topics and will be created with the assistance of the expert advisory board.

The experts are also available in the Expert Room where Attendees may ask questions.

E-Commerce Room

The E-Commerce Room limits purchases to specific authorized buyers. Each buyer is verified and authenticated by various methods including but not limited to a screening process that compares the buyer's state medical license number and the buyer's DEA number with an up-to-date database that contains both. In addition, after each buyer is verified and authenticated, each buyer must have an approved method of payment such as ("EFT") Electronic Funds Transfer, Business Credit Card, Debit Card or other method of payment.

The virtual Medtradeshow will track the receipt of information ordered while on-site, send an e-mail confirming order placed by the purchaser, send an e-mail to the purchaser when the items have been shipped, and provide each Attendee with an opportunity to obtain information in another room.

Continuing Education Room

The Continuing Education room provides each Attendee with an opportunity to register for special programs, dinner lectures or virtual continuing education activities for Attendees. The Attendees will obtain continuing education credits for attending lectures, workshops, and symposia. The Continuing Education room also provides opportunities of obtaining continuing education via newsletters, books, audiotapes, videotapes, monographs and supplements. In particular, the information provided in the Continuing Education room is not controlled or influenced by any manufacturers of medical equipment, devices, or pharmaceutical products. Such a characteristic distinguishes the Continuing Education room from the Category II Detailing Room and the E-Commerce Room.

The Continuing Education room is developed with input from Special Advisory Panels and from input from the Attendees as to what information they wish to learn about (also known as Needs Assessment). In the physical world, continuing education programs focus on the appropriateness of clinical decision making and implementation of these decisions which are condition specific, procedure specific, or address important functions of patient care, such as medication use, infection control, patient assessment, etc. The Continuing Education Programs are designed to evaluate the processes or outcomes of care associated with the delivery of clinical services and/or pharmaceutical products and/or medical equipment in order to continuously improve patient health outcomes. This invention is unique in the use of advisory panels and Attendees' needs assessments to help design the events occurring in the continuing education room.

The Continuint Education room will also allow an authorized Attendee to sign up to attend a live continuing education program in person at the location that such program is being conducted.

The Continuing Education room also includes Post Medtradeshow Features, such as satisfaction surveys, request for suggestions on improvements, information on future continuing education programs, information on other present continuing education programs that may be of interest to the Attendee, tracking receipts of goods and services and the rewarding of continuing education credits, request e-mails on various topics, including, but not limited to, documents or information that may be related to areas that such Attendee visited.

Case Conference Room

The Case Conference Room is a part of the convention floor and is designed to include, but not limited to, the presentation of case reports. These cases will be prepared by experts who will use them to demonstrate key elements in the diagnosis and treatment of a particular disease, syndrome, drug reaction, allergy, injury or other medically related problem. Those visiting this room will learn about the particulars of the cases. Situational variables surrounding each case may be different. Cases that may appear similar at first, when examined more closely reveal themselves to be different due to differences in time, location, conditions, and individuals involved.

In addition, the presentations can be structured to allow the expert to propose a diagnosis and treatment regimen that can then be compared to that proposed by the Attendee. The access can be either synchronous or asynchronous. Synchronous accesses allow interaction between expert(s) and Attendee(s)to take place simultaneously. On the other hand, asynchronous accesses allow experts and or/Attendees to respond at their own convenience.

Office Management Room

It provides a forum for Attendees to obtain office practice information, systems, policies, procedures, software, reimbursement information, medical record information, bill information, and opinions on how to manage means and solve problems in terms of their office practices or other managerial activities except disease management which will be treated separately in the Disease Management room.

Disease Management Room

Disease Management is a program that will include a treatment process for various disease states that generally includes physician or healthcare professional participation.

It generally is a broad approach to appropriate coordination of the entire disease treatment process that often involves shifting away from more expensive inpatient and acute care to areas such as medication compliance, diet compliance, preventive medicine, patient counseling and education, and outpatient care. The Disease Management room provides a process for Attendees to better manage the treatment of patients. As with the Continuing Education room, the information provided in the Disease Management room is not controlled by or influenced by any manufacturers of medical equipment, devices, or pharmaceutical products.

Tele-Medicine Room

Tele-medicine provides access to healthcare professionals via telecommunications technology to more expert healthcare professionals who can assist in the treatment of a patient. Such a characteristic distinguishes the Tele-Medicine Room from the Case Conference Room and the Continuing Education room.

Post Medtradeshow Feature

All data collected by Medtradeshow will be assembled, stored, correlated or otherwise processed for Medtradeshow in accordance with all Federal and State Privacy and Confidentiality Laws and Regulations.

Participants may choose to receive follow up information, answer surveys and questionnaires and track their transactions or interests via communication vehicles in conjunction with the optional features of concierge, e-LERTS, detailing, celebrity Pop-Ups, Case conferencing, Tele-Medicine, Continuing Education, Use of Advisory Panels, Needs Assessment, Office Management and Disease Management. For example, through e-LERTS, the invention provides each authorized Attendee, after their departure from the site, the opportunity to purchase authorized products and services and order copies of enduring materials. In addition, the combination of input from the experts, advisory panels along with suggestions from Attendees as to what subjects they feel need addressing will provide an important objective element to update the operation of the Medtradeshow.

What is claimed is:

1. A system for providing a completely virtual healthcare industry trade show via internet, comprising:
  at least one server computer for providing healthcare sources of information, products or services desired by participants of the healthcare industry trade show, said at least one server computer having an access-limiting software element for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so as to ensure that each of said participants of the healthcare industry and said attendees is appropriately authorized to conduct transactions of access-limited information, products or services with other so authorized participants of the healthcare industry trade show or attendees;
  at least one other computer used by any of said participants of the healthcare industry connected via internet or intranet to said at least one server computer to conduct transactions via said healthcare industry trade show; and
  a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show,
  wherein communication between any of said healthcare sources and participants of the healthcare industry facilitated through said at least one server computer with said attendees and others of said participants of the healthcare industry uses any of said plurality of communication vehicles, at the option of any of said participants of the healthcare industry or said attendees, whereby said communication between said healthcare sources, said participants and said attendees form a virtual trade show independent of any non-virtual activities in the healthcare industry.

2. A system for providing a completely virtual healthcare industry trade show via internet according to claim 1, wherein said at least one server computer is equipped with an artificial intelligence software component.

3. A system for providing a completely virtual healthcare industry trade show via internet according to claim 2, wherein said artificial intelligence software component includes a multiple-language processing means for translating data on the information, products or services available through said healthcare trade show into a language selected by one of said participants of the healthcare industry.

4. A system for providing a completely virtual health care industry trade show via internet according to claim 1, wherein said at least one server computer includes at least one of:
  (a) A concierge software module for providing general or specific information about said health care industry trade show;
  (b) An eLERTS software module for providing electronic instant messages for information about products, services, articles, symposia, and booth content;
  (c) An electronically created celebrity "pop-ups" software module for facilitating spontaneous interactions between at least one expert of the health care industry and at least one of said participants and attendees of the health care industry;
  (d) An electronically created E-commerce certifying feature software module for certifying the financial credit of a party of to any transactions conducted in the said E-commerce room;
  (e) An electronically created E-commerce certifying feature software module for certifying the creditability of the representations of a party of said transactions;
  (f) An electronically created E-commerce tracking software module for tracking the receipt and execution of orders, shipments of goods/delivery of services, and payments;
  (g) A Post Visit software module for facilitating each said attendee's receipt of follow-up information, surveys and questionnaires as well as track said transactions or interests via said communication vehicles;
  (h) An input signal support software module for said communication vehicles wherein signals are inputted by said participant via inputting means which includes a touch screen, a keyboard, a handwriting recognition means, or a voice recognition means; and
  (i) An image display support software module for said communication vehicles for supporting textual, 2-D or 3-D imagery signals to be displayed at said at least one other computer used by said participant.

5. A system for providing a completely virtual healthcare industry trade show via internet according to claim 4, wherein at least (a) is provided.

6. A system for providing a completely virtual healthcare industry trade show via internet according to claim 5, wherein said concierge software module includes a software component for generating a concierge image that appears as a figure of any sex, race, height, weight, eye or hair color.

7. A system for providing a completely virtual healthcare industry trade show via internet according to claim 5, wherein said concierge software module records and captures the activities of each of said attendees.

8. A system for providing a completely virtual healthcare industry trade show via internet according to claim 5, wherein said concierge software module records and reports the activities of a visiting participant to said system.

9. A system for providing a completely virtual heathcare industry trade show via internet according to claim 7, wherein said concierge software module, with appropriate consents and compliance with state and federal privacy and confidentiality laws, provides either compiled data or specific data to one or more exhibitors.

10. A system for providing a completely virtual healthcare industry trade show via internet according to claim 5, wherein said concierge determines software module is formed to determine each attendee's special interest and help each of said attendees find specific information, locations, or areas of interest within said completely virtual healthcare industry trade show.

11. A system for providing a completely virtual healthcare industry trade show via internet according to claim 5, wherein said concierge provides software module is formed to provide each of said attendees with a history of any of each such attendee's previous visits.

12. A system for providing a completely virtual healthcare industry trade show via internet according to claim 5, wherein said concierge software module is formed to provide each of said attendees with information regarding specific products or services.

13. A system for providing a completely virtual healthcare industry trade show via internet according to claim 5, wherein said concierge software module is formed to provide each of said attendees with an update on what is new at the virtual healthcare trade show since each said attendee's last visit.

14. A system for providing a completely virtual healthcare industry trade show via internet according to claim 4, wherein at least (c) is provided.

15. A system for providing a completely virtual healthcare industry trade show via internet according to claim 14, wherein said at least one expert randomly pops up on the floor of said virtual healthcare industry trade show to communicate with attendees.

16. A system for providing a completely virtual healthcare industry trade show via internet according to claim 4, wherein at least (d) is provided.

17. A system for providing a completely virtual healthcare industry trade show via internet according to claim 4, wherein at least (e) is provided.

18. A system for providing a completely virtual healthcare industry trade show via internet according to claim 4, wherein at least (f) is provided.

19. A system for providing a completely virtual healthcare industry trade show via internet according to claim 4, wherein at least (b) is provided.

20. A system for providing a completely virtual healthcare industry trade show vial internet according to claim 4, wherein at least (g) is provided.

21. A system for providing a completely virtual healthcare industry trade show via internet according to claim 4, wherein at least (h) is provided.

22. A system for providing a completely virtual healthcare industry trade show via internet according to claim 21, wherein said signals are displayed via animation or virtual reality.

23. A system for providing a completely virtual healthcare industry trade show via internet according to claim 5, wherein at least (i) is provided.

24. A system for providing a completely virtual healthcare industry trade show via internet according to claim 1, wherein said healthcare sources include at least one of:
   (a) a detailing service source for promoting at least one exhibitor of said health care industry trade show;
   (b) an expert room service source for providing access to at least one expert available to answer questions from said participants of the health care industry and said attendees;
   (c) a case conferencing service source for presenting at least one case report to at least one of said participants and said attendees of the health care industry;
   (d) an advisory panel service source for providing input from experts in the healthcare industry as to what content to present;
   (e) a need assessment process source where said participant and said attendees input suggested subjects they want to learn more about;
   (f) a continuing education service source for providing continuing education for said participants of the health care industry and said attendees;
   (g) a tele-medicine service source for delivering tele-medicine by said participants of the health care industry;
   (h) an office management service source for exchanging information regarding managerial activities among said participants of the health care industry and said attendees;
   (i) a disease management service source for exchanging information regarding disease management activities among said participants of the health care industry and said attendees;
   (i) a grand rounds service source for providing interactive ground rounds communication; and
   (k) a speaker bureau service source for said participants to offer lecturing services to other participants and said attendees about a variety of topics including but not limited to the diagnosis and treatment of a particular disease.

25. A system for providing a completely virtual healthcare industry trade show via internet according to claim 24, is provided.

26. A system for providing a completely virtual healthcare industry trade show via internet according to claim 25, wherein said at least one exhibitor of said virtual-healthcare industry trade shows provides information about products or services or their combinations, that conform to FDA labeling requirements.

27. A system for providing a completely virtual healthcare industry trade show via internet according to claim 25, wherein said at least one exhibitor of said virtual healthcare industry trade show provides "off-label" products, services or their combinations that do not conform to FDA labeling requirements.

28. A system for providing a completely virtual healthcare industry trade show via internet according to claim 24, wherein at least (b is provided.

29. A system for providing a completely virtual healthcare industry trade show via internet according to claim 28, where said healthcare source of said expert room service having at least one expert is formed such that said attendee chooses from a series of programmed questions to ask said at least one expert.

30. A systems for providing a completely virtual healthcare industry trade show via internet according to claim 28, where an said healthcare source of said expert room service having at least one expert is formed such that said attendee raises spontaneous questions to at least one expert.

31. A system for providing a completely virtual healthcare industry trade show via internet according to claim 24, wherein at least (c) is provided.

32. A system for providing a completely virtual healthcare industry trade show via internet according to claim 31, said healthcare source of said Case Conferencing feature is formed such that at least one case report is presented to demonstrate key elements in the diagnosis and treatment of a particular healthcare problem.

33. A system for providing a completely virtual healthcare industry trade show via internet according to claim 31, said information resource of said Case Conferencing feature is formed such that said attendee has the opportunity to provide input including proposing another diagnosis and treatment.

34. A system for providing a completely virtual healthcare industry trade show via internet according to claim 24, wherein at least (d) is provided.

35. A system for providing a completely virtual healthcare industry trade show via internet according to claim 34, said healthcare source of said Advisory Panels feature is formed such that needs assessments are used to help said Advisory Panels feature to design future events.

36. A system for providing a completely virtual healthcare industry trade show via internet according to claim 24, wherein at least (e) is provided.

37. A system for providing a completely virtual healthcare industry trade show via internet according to claim 24, wherein at least (f) is provided.

38. A system for providing a completely virtual healthcare industry trade show via internet according to claim 37, said healthcare source of the Continuing Education service source is formed to not be controlled or influenced by any manufacturers of medical equipment, devices or pharmaceutical products.

39. A system for providing a completely virtual healthcare industry trade show via internet according to claim 37, said healthcare source of the Continuing Education service source includes being formed to provide satisfaction surveys or request for suggestions on improvements.

40. A system for providing a completely virtual healthcare industry trade show via internet according to claim 37, said healthcare source of the Continuing Education service source includes being formed to provide tracking receipts of educational credits and materials.

41. A system for providing a completely virtual healthcare industry trade show via internet according to claim 37, said healthcare source of the Continuing Education service source includes receiving from the being formed to receive from said attendees e-mails on various topics.

42. A system for providing a completely virtual healthcare industry trade show via internet according to claim 24, wherein at least (g) is provided.

43. A system for providing a completely virtual healthcare industry trade show via internet according to claim 24, wherein at least (h) is provided.

44. A system for providing a completely virtual healthcare industry trade show via internet according to claim 24, wherein at least (i) is provided.

45. A system fore providing a completely virtual healthcare industry trade show via internet according to claim 44, said healthcare source of the Disease Management service source is formed to provide said attendees with information about special disease states, conditions or specialties.

46. A system for providing a completely virtual healthcare industry trade show via internet according to claim 24, wherein at least (i) is provided.

47. A system for providing a completely virtual healthcare industry trade show via internet according to claim 46, wherein said interactive grand rounds communications are moderated by at least one expert to explain suggested diagnosis and treatment.

48. A system for providing a completely virtual healthcare industry trade show via internet according to claim 24, wherein at least (k) is provided.

49. A system for providing a completely virtual healthcare industry trade show via internet according to claim 1, wherein said access-determining credential data include at least one of Drug Enforcement Administration provider numbers, a Medical Education Number and a State License Number.

50. A system via an internet site that is independent from participants including manufacturers, wholesalers, and distributors of health related products and services for promoting and marketing said health related products and services in a completely virtual trade show environment, comprising:

at least one server computer for providing healthcare sources of information, products or services desired by participants of the healthcare industry trade show, said at least one server computer having an access-limiting software element for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so as to ensure that each of said participants of the healthcare industry and said attendees is appropriately authorized to conduct transactions of access-limited information, products or services with other so authorized participants of the healthcare industry trade show or attendees;

at least one other computer used by any of said participants of the healthcare industry connected via internet or intranet to said at least one server computer to conduct transactions via said healthcare industry trade show; and a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show, wherein communication between any of said healthcare sources and participants of the healthcare industry facilitated through said at least one server computer with said attendees and others of said participants of the healthcare industry uses any of said plurality of communication vehicles, at the option of any of said participants of the healthcare industry or said attendees, whereby said communication between said healthcare sources, said participants and said attendees form a virtual trade show independent of any non-virtual activities in the healthcare industry.

51. A system, according to claim 50, wherein said communication between said attendees and said healthcare information sources is formed to include where an authorized attendee can request an office detail visit from a manufacturer's representative.

52. A system, according to claim 50, wherein said communication between said attendee and said healthcare information sources is formed to include where an authorized attendee can request and receive product information.

53. A system, according to claim 50, wherein said communication between said attendee and said healthcare information sources, is formed to include where an authorized attendee can request and receive a product monograph.

54. A system according to claim 50, wherein request and receipt of said product monograph includes promotional or marketing materials that are available on demand, at scheduled times or to be physically shipped to the attendee.

55. A system, according to claim 50, wherein said communication between said attendee and said healthcare information sources is formed to include where an authorized attendee can request and receive a product sample.

56. A system, according to claim 50, wherein said communication between said attendee and said healthcare information sources is formed to include where an authorized attendee can request a health related audio.

57. A system according to claim 56, wherein request and receipt of said health related audio includes promotional or marketing materials are available on demand, at scheduled times or to be physically shipped to the attendee.

58. A system, according to claim 50, wherein said communication between said attendee and said healthcare information sources is formed to include where an authorized attendee can request a health related video.

59. A system according to claim 58, wherein request and receipt of said health related video includes promotional or marketing materials are available via on demand, at scheduled times or to be physically shipped to the attendee.

60. A system, according to claim 50, wherein said communication between said attendee and said healthcare information sources is formed to include where an authorized attendee can request a health related abstract.

61. A system, according to claim 50, wherein said communication between said attendee and said healthcare information sources is formed to include where an authorized attendee can request a health related reprint.

62. A system, according to claim 50, wherein said communication between said attendee and said healthcare information sources is formed to include where an authorized attendee can request a health related newsletter.

63. A system according to claim 62, wherein request and receipt of said health related newsletter includes promotional or marketing materials are available on demand, at scheduled times or to be physically shipped to the attendee.

64. A system, according to claim 50, wherein said communication between said attendee and said healthcare information sources is formed to include where an authorized attendee can request a health related monograph.

65. A system according to claim 64, wherein request and receipt of said health related monograph includes promotional or marketing materials are available on demand, at scheduled times or to be physically shipped to the attendee.

66. A system, according to claim 50, wherein said communication between said attendee and said healthcare information sources is formed to include where an authorized attendee can request a health related slide kit.

67. A system according to claim 66, wherein request and receipt of said health related slide kit includes promotional or marketing materials are available on demand, at scheduled times or to be physically shipped to the attendee.

68. A system, according to claim 50, wherein said communication between said attendee and said healthcare information sources is formed to include where an authorized attendee can request a health related supplement.

69. A system according to claim 68, that such wherein request and receipt of said health related supplement includes promotional or marketing materials are available on demand, at scheduled times or to be physically shipped to the attendee.

70. A system, according to claim 50, wherein said communication between said attendee and said healthcare information sources is formed to include where an authorized attendee can register for a continuing medical education program.

71. A system, according to claim 50, wherein said communication between said attendee and said healthcare information sources is formed to include where an authorized attendee can attend a pre-recorded continuing education program that is available on demand or at a scheduled time.

72. A system, according to claim 50, wherein said communication between said attendee and said healthcare information resources is formed to include where an authorized attendee can attend a live continuing education program that is available at a scheduled time.

73. A system, according to claim 50, wherein said communication between said attendee and said healthcare information resources is formed to include where an authorized attendee can register for a physical CME program.

74. A system, according to claim 50, wherein said communication between said attendee and said healthcare information resources is formed to include where an authorized attendee has an option to register for a special program or programs.

75. A system, according to claim 50, wherein said communication between said attendee and said healthcare information resources is formed to include where an authorized attendee has an option to register for a special program or clinical trials.

76. A system, according to claim 50, wherein said communication between said attendee and said healthcare information resources is formed to include where an authorized attendee has an option to register for a special program or special studies.

77. A system, according to claim 50, wherein said communication between said attendee and said healthcare information resources is formed to include where an authorized attendee has an option to register for a special program to be a speaker or member of a speaker's bureau.

78. A system, according to claim 50, wherein said communication between said attendee and said healthcare information resources is formed to include where an authorized attendee has an option to register for a special program or to participate in grand rounds.

79. A system, according to claim 50, wherein said communication between said attendee and said healthcare information resources is formed to include where an authorized attendee has an option to register for a special program or to participate in an advisory board.

80. A system, according to claim 50, wherein said communication between said attendee and said healthcare information resources is formed to include where an authorized attendee has an option to either participate or observe in special program or programs, clinical trials, special studies, membership of a speaker's bureau, participate in grand rounds or to participate on an advisory board.

81. A system according to claim 50, wherein said healthcare information resources include promotional or marketing materials being available on demand, at scheduled times or to be physically shipped to an attendee.

82. A system according to claim 50, that such wherein said healthcare information resources include promotional or marketing materials are available on demand, at scheduled times or to be physically shipped to the attendee.

83. A system for providing a completely virtual healthcare industry trade show via internet according to claim 50, wherein said healthcare information sources include at least one of medical journals, company data, product information, information from drug trials, expert advisors, information from meetings, grand rounds, and promotional-materials.

84. A method for providing a completely virtual healthcare industry trade show via internet, comprising the steps of:

providing healthcare information sources, products or services desired by an attendee of the healthcare industry trade show via at least one server computer;

providing access-limiting software element tangibly embodied on said at least one server computer for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so as to ensure that each of said participants of the healthcare industry and said attendees is appropriately authorized to conduct transactions of access-limited information, products or services with other so authorized participants of the healthcare industry trade show or attendees;

providing at least one other computer used by said attendee of the healthcare industry trade show connected via internet or intranet to said at least one server computer to conduct transactions via said healthcare industry trade show;

providing a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show; and forming and thereby operating said virtual healthcare industry trade show independent of any non-virtual activity in the healthcare industry trade show by facilitating the communication between said attendee with at least one of said healthcare information sources and other attendees via said at least one server computer either using any of said at least one other computer and internet or using said plurality of communication vehicles via the internet at the option of any of said attendee or other attendees.

85. The method according to claim 84, further comprising a step of interacting with said attendee with artificial intelligence.

86. The method according to claim 84, wherein said step of forming and operating said virtual healthcare industry trade show further comprising includes a step of interacting with said attendee with artificial intelligence.

87. The method according to claim 86, wherein said step of facilitating communication includes a step of randomly popping up at least one expert supported by the artificial intelligence on the floor of said healthcare industry trade show to communicate with attendees.

88. The method according to claim 87, wherein said step of facilitating communication further includes a step of providing said attendee a series of programmed questions to ask said at least one expert.

89. The method according to claim 87, wherein said step of facilitating communication further includes a step of taking spontaneous questions-raised by said attendee to said at least one expert.

90. The method according to claim 84, wherein said step of forming and operating said virtual healthcare industry trade show further comprising includes a step of translating text inputted by said attendee into a language selected by said attendee.

91. The method according to claim 84, wherein said step of forming and operating said virtual healthcare industry trade show includes electronically creating at least one of:

(a) a concierge feature for providing general or specific information about said health care industry trade show;

(b) an eLERTS feature for providing electronic instant messages for information about products, services, articles, symposia, and booth content;

(c) a celebrity "pop-ups" feature for facilitating spontaneous interactions between at least one expert of the health care industry and at least one of said participants of the health care industry;

(d) an E-commerce room certifying feature for certifying the financial credit of a party of to any transactions conducted in the said E-commerce room;

(e) an E-commerce room certifying feature for certifying the creditability of the representations of a party of said transactions;

(f) an E-commerce room tracking feature for tracking the receipt and execution of orders, shipments of goods/delivery of services, and payments;

(g) a Post Visit feature for facilitating each said attendee's receipt of follow-up information, surveys and questionnaires as well as track said transactions or interests via said communication vehicles.

92. The method according to claim 84, wherein said step of forming and operating said virtual healthcare industry trade show further includes a step of supporting signals inputted by said attendee via a touch screen, a keyboard, a handwriting recognition means, or a voice recognition means.

93. The method according to claim 92, wherein said signals are displayed via animation or virtual reality.

94. The method according to claim 84, wherein said step of forming and operating said virtual healthcare industry trade show further includes a step of displaying textual, 2-D or 3-D imagery signals in response to said communication between said attendee and at least one of said healthcare information sources and other attendees.

95. The method according to claim 94, wherein said signals are displayed via animation or virtual reality.

96. The method according to claim 84, wherein said step of facilitating communication further includes a step of presenting said concierge as a figure of any sex, race, height, weight, eye or hair color.

97. The method according to claim 84, wherein said step of forming and operating said virtual healthcare industry trade show further includes a step of recording and capturing the activities of said attendee.

98. The method according to claim 84, wherein said step of forming and operating said virtual healthcare industry trade show further includes a step of providing either compiled data or specific data to one or more Exhibitors with appropriate consents and compliance with state and federal privacy and confidentiality laws.

99. The method according to claim 84, wherein said step, of facilitating communication further includes steps of determining special interest of said attendee and assisting said attendee to find specific information, locations, or areas of interest from the information resources within said healthcare industry trade show.

100. The method according to claim 84, wherein said step of forming and operating said virtual healthcare industry trade show further includes a step of providing said attendee with a history of any of said attendee's previous visits.

101. The method according to claim 84, wherein said step of forming and operating said virtual healthcare industry trade show further includes a step of providing said attendee with information regarding specific products or services.

102. The method according to claim 84, wherein said step of forming and operating said virtual healthcare industry trade show further includes a step of providing said attendee with an update on what is new at the virtual healthcare industry trade show since said attendee's last visit.

103. The method according to claim 84, wherein said step of forming and operating said virtual healthcare industry trade show further includes a step of facilitating at least one Exhibit or of said health care industry trade show to provide an information resource about products or services or their combinations, that conform to FDA labeling requirements.

104. The method according to claim 84, wherein said step of forming and operating said virtual healthcare industry trade show further includes a step of facilitating at least one Exhibitor (non-manufacturer) of said healthcare industry trade show to provide "off-label" products, services or their combinations that does not conform to the FDA labeling-requirements.

105. The method according to claim 84, wherein said step of facilitating communication includes a step of presenting at least one case report to demonstrate key elements in the diagnosis and treatment of a particular healthcare problem.

106. The method according to claim 105, wherein said step of facilitating communication includes a step of receiving input proposed by said attendee regarding another diagnosis and treatment.

107. The method according to claim 84, wherein said step of facilitating communication includes a step of conducting needs assessments to design future events.

108. The method according to claim 84, wherein said step of facilitating communication includes a step of providing Continuing Education to said attendee which is not controlled or influenced by any manufacturers of medical equipment, devices or pharmaceutical products.

109. The method according to claim 84, wherein said step of facilitating communication includes steps of providing Continuing Education to said attendee, and conducting satisfaction surveys or request for suggestions on improvements.

110. The method according to claim 84, wherein said step of facilitating communication includes steps of providing Continuing Education to said attendee, and tracking receipts of educational credits and materials.

111. The method according to claim 84, wherein said step of facilitating communication includes steps of providing Continuing Education to said attendee, and receiving from said attendee e-mails on various topics.

112. The method according to claim 84, wherein the access-determining credential data includes DEA provider numbers, ME numbers and/or State License numbers.

113. The method according to claim 84, wherein said step of providing said healthcare information sources includes electronically creating at least one of:

(a) a detailing service, source for promoting at least one exhibitor of said health care industry trade show;

(b) an expert room service source for providing access to at least one expert available to answer questions from said participants of the health care industry and said attendees;

(c) a case conferencing service source for presenting at least one case report to at least one of said participants and said attendees of the health care industry;

(d) an advisory panel service source for providing input from experts in the healthcare industry as to what content to present;

(e) a need assessment process source where said participant and said attendees input suggested subjects they want to learn more about;

(f) a continuing education service source for providing continuing education for said participants of the health care industry and said attendees;

(g) a tele-medicine service source for delivering tele-medicine by said participants of the health care industry;

(h) an office management service source for exchanging information regarding managerial activities among said participants of the health care industry and said attendees;

(i) a disease management service source for exchanging information regarding disease management activities among said participants of the health care industry and said attendees;

(j) a ground rounds service source for providing interactive ground rounds communication; and (k) a speaker bureau service source for said participants to offer lecturing services to other participants and said attendees about a variety of topics including but not limited to the diagnosis and treatment of a particular disease.

114. The method according to claim 113, wherein the Disease Management service source provides attendees with information about special disease states, conditions or specialties.

115. The method according to claim 113, wherein the interactive grand rounds communications are moderated by at least one expert to explain suggested diagnosis and treatment.

116. A method for promoting and marketing health related products and services via an internet or intranet site that is independent from participants including manufacturers, wholesalers, and distributors of said health related products and services, comprising:

providing healthcare information sources, products or services desired by an attendee of the healthcare industry trade show via at least one server computer;

providing access-limiting software element tangibly embodied on said at least one server computer for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so as to ensure that each of said participants of the healthcare industry and said attendees is appropriately authorized to conduct transactions of access-limited information, products or services with other so authorized participants of the healthcare industry trade show or attendees;

providing at least one other computer used by said attendee of the healthcare industry trade show connected via internet or intranet to said at least one server computer to conduct transactions via said healthcare industry trade show;

providing a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show; and forming and thereby operating said virtual healthcare industry trade show independent of any non-virtual activity in the healthcare industry trade show by facilitating the communication between said attendee with at least one of said healthcare information sources and other attendees via said at least one server computer either using any of said at least one other computer and internet or using said plurality of communication vehicles via the internet at the option of any of said attendee or other attendees.

117. The method according, to claim 116, wherein said step of facilitating communication further includes a step of providing an authorized attendee via the Internet a pre-recorded continuing education program that is available on demand or at a scheduled time.

118. The method according to claim 116, wherein said step of facilitating communication further includes a step of providing an authorized attendee an office detail visit from a manufacturer's representative.

119. The method according to claim 116, wherein said step of facilitating communication further includes a step of providing an authorized attendee product information.

120. The method according to claim 116, wherein said step of facilitating communication further includes a step of providing an authorized attendee a product monograph or a product sample.

121. The method according to claim 116, wherein said step of facilitating communication further includes a step of providing an authorized attendee a health related audio, video, abstract, reprint, newsletter, monograph, slide kit, or supplement.

122. The method according to claim 116, wherein said step of facilitating communication further includes a step of registering an authorized attendee for a continuing medical education program.

123. The method according to claim 116, wherein said step of facilitating communication further includes a step of providing an authorized attendee via the Internet a live continuing education program that is available at a scheduled time.

124. The method according to claim 116, wherein said step of facilitating communication further includes a step of registering an authorized attendee for a special program as a speaker or as a member of a speaker's bureau.

125. The method according to claim 116, wherein said step of facilitating communication further includes a step of accepting an authorized attendee to participate in grand rounds.

126. The method according to claim 116, wherein said step of facilitating communication further includes a step of making promotional or marketing materials available via the Internet on demand, at scheduled times, or to be physically shipped to the attendee.

127. The method according to claim 116, wherein sources of the information resources include at least one of medical journals, company data, product information, information from drug trials, expert advisors, information from meetings, grand rounds, or promotional materials.

* * * * *